(12) United States Patent
Kirst et al.

(10) Patent No.: US 11,954,718 B1
(45) Date of Patent: Apr. 9, 2024

(54) PERSONALIZATION SYSTEM

(71) Applicant: MWG, LLC, Woodside, CA (US)

(72) Inventors: Jonathan S. Kirst, Oakland, CA (US); John R. Kirst, Woodside, CA (US); John Edward Duffy, San Jose, CA (US); Xiaowei Li, Pleasanton, CA (US); Kenneth E Waln, Los Altos, CA (US)

(73) Assignee: MWG, LLC, Woodside, CA (US)

( * ) Notice: Subject to any disclaimer, the term of this patent is extended or adjusted under 35 U.S.C. 154(b) by 0 days.

(21) Appl. No.: 17/868,002

(22) Filed: Jul. 19, 2022

Related U.S. Application Data

(63) Continuation of application No. 17/013,571, filed on Sep. 5, 2020, now Pat. No. 11,423,459.

(60) Provisional application No. 62/896,933, filed on Sep. 6, 2019.

(51) Int. Cl.
*G06Q 30/00* (2023.01)
*A01H 5/08* (2018.01)
*G06F 16/9535* (2019.01)
*G06Q 30/0601* (2023.01)

(52) U.S. Cl.
CPC .......... *G06Q 30/0627* (2013.01); *A01H 5/08* (2013.01); *G06F 16/9535* (2019.01); *G06Q 30/0613* (2013.01); *G06Q 30/0629* (2013.01)

(58) Field of Classification Search
None
See application file for complete search history.

(56) References Cited

U.S. PATENT DOCUMENTS

| | | |
|---|---|---|
| 8,751,429 B2 | 6/2014 | Dillon et al. |
| 8,782,042 B1 | 7/2014 | Cooke et al. |
| 9,026,484 B2 | 5/2015 | Dillon et al. |
| 9,449,077 B2 | 9/2016 | Dillon et al. |
| 10,102,298 B2 | 10/2018 | Madisch et al. |
| 10,102,559 B1 | 10/2018 | Jain et al. |
| 10,127,598 B2 | 11/2018 | Dillon et al. |
| 10,460,246 B2 | 10/2019 | Dillon et al. |
| 2002/0165790 A1 | 11/2002 | Bancroft et al. |
| 2010/0205045 A1 | 8/2010 | Zhang et al. |
| 2012/0226698 A1 | 9/2012 | Silvestre et al. |
| 2013/0339348 A1 | 12/2013 | Pickelsimer |
| 2014/0324624 A1 | 10/2014 | Ward et al. |
| 2015/0046471 A1 | 2/2015 | Tompkins |
| 2015/0378971 A1 | 12/2015 | Fischer |
| 2016/0055563 A1 | 2/2016 | Grandhi |
| 2016/0147891 A1 | 5/2016 | Chhichhia et al. |
| 2018/0082032 A1 | 3/2018 | Allen et al. |
| 2018/0293644 A1 | 10/2018 | Allen et al. |
| 2018/0349977 A1 | 12/2018 | Codella et al. |
| 2020/0057950 A1 | 2/2020 | Dillon et al. |
| 2021/0319346 A1 | 10/2021 | Dillon et al. |
| 2021/0334879 A1 | 10/2021 | Sussman et al. |
| 2022/0108556 A1 | 4/2022 | Peng et al. |

OTHER PUBLICATIONS

Martinez et al., Grapevine: A Wine Prediction Algorithm Using Multo-dimensional Clustering Methods, Jun. 29, 2018, arXiv:1807. 00692, pp. 1-5.

*Primary Examiner* — Naeem U Haq
(74) *Attorney, Agent, or Firm* — Offit Kurman, P.A.; Gregory A. Grissett

(57) ABSTRACT

An embodiment of the present disclosure a system and method for extracting items of information, such as wine from a wine list of a commercial establishment.

40 Claims, 7 Drawing Sheets

PERSONALIZATION SYSTEM

CROSS-REFERENCE TO RELATED APPLICATIONS

The present application is a continuation of U.S. application Ser. No. 17/013,571, filed Sep. 5, 2020, which claims the benefit of and priority U.S. Provisional Application No. 62/896,933, filed on Sep. 6, 2019, the entire disclosures of which is incorporated by reference into the present application.

TECHNICAL FIELD

The present disclosure relates to a recommendation system and related methods.

SUMMARY

An embodiment of the present disclosure is a method for extracting from a list of a commercial establishment. On one example, the list is a wine list. The method includes accessing with a communications network an electronic version of a wine list for one or more commercial establishment. The method also includes converting the electronic version of the wine list into a wine list text file. The method also includes parsing the wine list text file to into lines of text including wine information. The method also includes parsing the lines of text into wine attributes for a plurality of wines on the wine list. The method also includes, based on the wine attributes for the plurality of wines, matching each of the plurality of wines on the wine list with one or more region-varietal pairs. Each region-varietal pair includes a geographic wine region and a wine varietal. The systems and methods as described herein are not limited for use with wine lists from restaurants. A wine list may come from any commercial establishment, such as wine store, alcohol store, grocery stores, and any other place where multiple wines are sold and/or consumed. In this disclosure, therefore, a retail establishment may include a restaurant, a store, a distributor, wholesaler, retailer, winery, vineyard, or any other physical location or e-commerce website.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings, illustrative embodiments of the disclosure. It should be understood, however, that the application is not limited to the precise arrangements and instrumentalities shown. In the drawings.

DETAILED DESCRIPTION OF ILLUSTRATIVE EMBODIMENTS

Embodiments of the present disclosure include a system, method, and related software applications for acquisition and analysis of preference data and item attribute data. The systems, methods, and related software applications as described herein may be used to recommend items from a list. For example, the systems, methods, and related software applications are configured for the acquisition and analysis of preference data and attribute data for wines. The systems, methods, and related applications as described herein may be used to recommend wine from wine lists of various commercial establishments, e.g. restaurants, wine stores, wineries, vineyards, retailers, distributors, etc. It should be appreciated that systems, methods and software applications are configured to recommend other items, such as chocolate, coffee, beer, whisky, cigars, etc.

Figure 1:
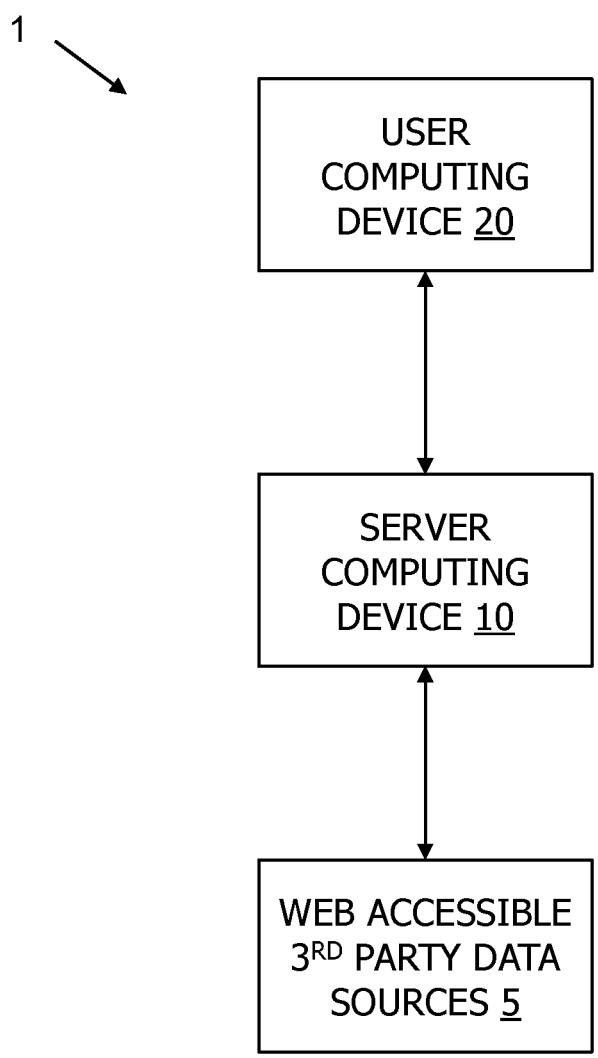
FIG. 1 is a diagram illustrating a system for recommending wine to a user, according to an embodiment of the present disclosure.

Referring to FIG. 1, an embodiment of the present disclosure is a system 1 including at least one server computing device 10, one or more user computing devices 20 in electronic communication with the server computing device 10, and one or more software applications 30 and 32 (FIGS. 2 and 3) implemented across computing devices 10 and 20. The software applications 30 and 32 are configured to, when executed, access third party data sources 5. In the present disclosure, third party data sources 5 may be wine data or wine attributes compiled from web accessible wine lists. A user computing device 20 may be associated with a different person or user. Accordingly, the system 1 is configured to acquire, analyze, and update wine preference data for a) an individual user or b) multiple users.

Software applications as described herein may be implemented over system components and configured to execute various steps in the methods described below. It should be appreciated that a software application can implement steps in the methods utilizing all of the system components or just portions of the system components. Furthermore, the software applications are described below in singular form. It should be appreciated that multiple software applications may interface to perform the described functions, and multiple applications can run on more than one computing device to implement the methodologies described herein.

Continuing with reference to FIG. 1, the system 1 is implemented via exemplary architecture that includes computing devices 10 and 20 in electronic communication with each other via a common communications network, such as, for example the Internet. As illustrated, the user computing device 20 and server computing device 10 are arranged in a client-server architecture. Such that each user computing device may access data from a server computing device "Access" or "accessing" as used herein can include retrieving information stored in memory on a computing device. For instance, "access" or "accessing" includes sending instructions via the network from server computing device 10 to computing device 20 so as to cause information to be transmitted to the memory of the computing device 20 for access locally by the computing device 20. In addition, or alternatively, "access" or "accessing" can include the server computing device 10 sending an instruction to computing device 20 to access information stored in the memory of the computing device 20. Reference to server computing device 10 and computing device 20 in this paragraph is exemplary and are used to only clarify use of words "access" or "accessing."

FIG. 1 illustrates a client-server network. But the software application can be implemented over any number of network configurations. For example, in alternate embodiments, the computing devices are configured as a peer-to-peer network architecture. In still other alternative embodiments, the computing devices can be arranged in a ring-type network architecture. Further, the software application can be implemented across computing devices arranged on a network that includes aspects of a client-server network, peer-to-peer network, ring-type network, and/or other network architectures known to a person of ordinary skill in the art. Accordingly, it should be appreciated that numerous suitable alternative communication architectures are envisioned.

Figure 2:
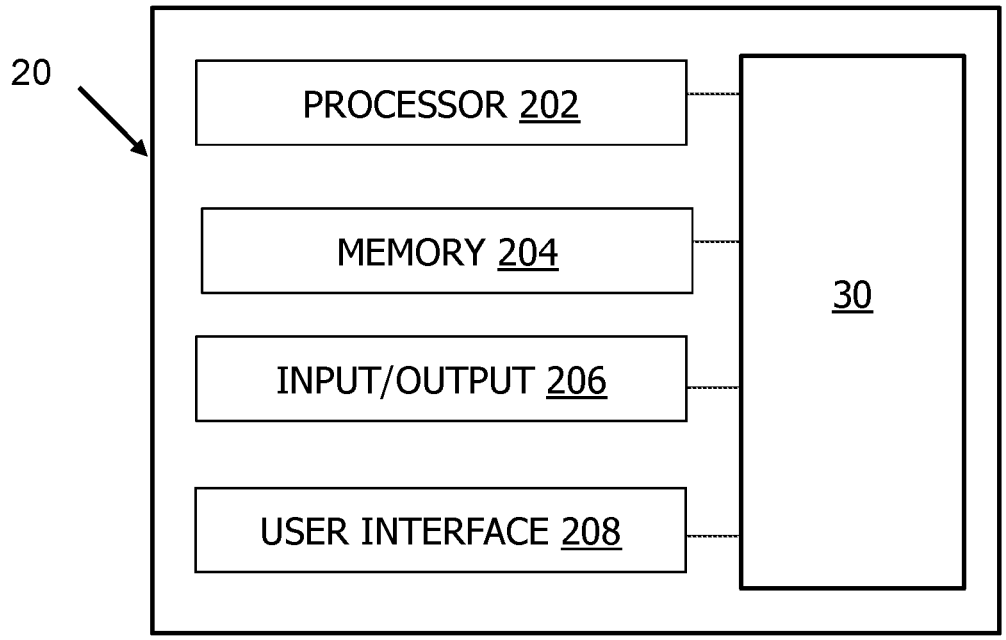
FIG. 2 is a computing device associated with each user illustrated in FIG. 1.

Turning to FIG. 2, the computing device 20 is configured to receive, process, and store various information used to implement one or more software applications, such as client software application 30. The hardware components of computing device 20 can include any appropriate device, examples of which include a portable computing device, such as a laptop, tablet or smart phone, or other computing devices, such as a desktop computing device or a server-computing device.

As illustrated in FIG. 2, the user computing device 20 includes one or more processors 22, a memory 24, an input/output 26, and a user interface (UI) 28. It is emphasized that the operation diagram depiction of the computing device 20 is exemplary and is not intended to imply a specific implementation and/or configuration. The processor 22, memory 24, input/output portion 26 and user interface 28 can be coupled together to allow communications therebetween and can interface with the software application 30. The software application 30 may include an application programmatic interface (API). As should be appreciated, any of the above components may be distributed across one or more separate computing devices.

Continuing with FIG. 2, the memory 24 can be volatile (such as some types of RAM), non-volatile (such as ROM, flash memory, etc.), or a combination thereof, depending upon the exact configuration and type of processor 22. The computing device 20 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic storage or other magnetic storage devices, universal serial bus (USB) compatible memory, or any other medium which can be used to store information and which can be accessed by the computing device 20.

Continuing with FIG. 2, in various embodiments, the input/output portion 26 includes an antenna or an electronic connector for wired connection, or a combination thereof. In some implementations, input/output portion 26 can include a receiver and transmitter, transceiver or transmitter-receiver. The input/output portion 26 can receive and/or providing information pertaining to communication with a network such as, for example, the Internet. As should be appreciated, transmit and receive functionality may also be provided by one or more devices external to computing device 20. For instance, the input/output portion 26 can be in electronic communication with a receiver.

Referring to FIG. 2, the user interface 28, which can include an input device and/or display (input device and display not shown) that allows a user to communicate with the computing device 20. The user interface 28 can include inputs that provide the ability to control the computing device 20, via, for example, buttons, soft keys, a mouse, voice actuated controls, a touch screen, movement of the computing device 20, visual cues (e.g., moving a hand in front of a camera on the computing device 20), or the like. The user interface 28 can provide outputs, including visual displays, such as exemplary display screens as illustrated in the enclosed appendix. Other outputs can include audio information (e.g., via speaker), mechanically (e.g., via a vibrating mechanism), or a combination thereof. In various configurations, the user interface 28 can include a display, a touch screen, a keyboard, a mouse, an accelerometer, a motion detector, a speaker, a microphone, a camera, or any combination thereof. The user interface 28 can further include any suitable device for inputting biometric information, such as, for example, fingerprint information, retinal information, voice information, and/or facial characteristic information, for instance, to require specific biometric information for access to the computing device 20. It should be appreciated that the computer devices can operate via any suitable operating system, such as Android, BSD, iOS, Linux, OS X, QNX, Microsoft Windows, Windows Phone, and IBM z/OS. Furthermore, the software application can operate with any of the operating systems.

Figure 3:
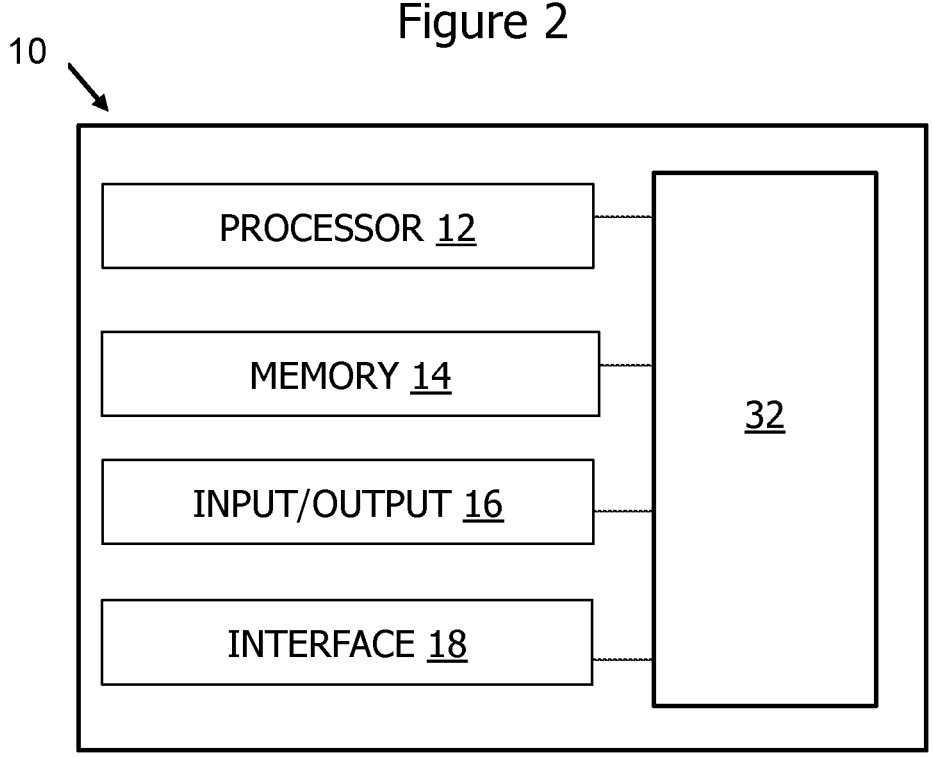
FIG. 3 is a server computing device illustrated in FIG. 1.

FIG. 3 is a diagram of the server computing device 10. The server computing device 10 includes one or more processors 12, a memory 14, an input/output 16, and a user interface (UI) 18, and on or more software applications, such as a server application 32. The processor 12, memory 14, input/output portion 16 and interface 18 can be coupled together to allow communications therebetween. As should be appreciated, any of the above components may be distributed across one or more separate server computing devices. The server computing device processor 12, memory 14, input/output 16, and interface 18 are similar to the processors 22, memory 24, input/output 26, and interface 28 described above with respect computing device 20. It should be appreciated that the server computer device can operate via any suitable operating system, such as Android, BSD, iOS, Linux, OS X, QNX, Microsoft Windows, Windows Phone, and IBM z/OS. It is emphasized that the operation diagram depiction of the server computing device 10 is exemplary and not intended to imply a specific implementation and/or configuration.

Figure 4:
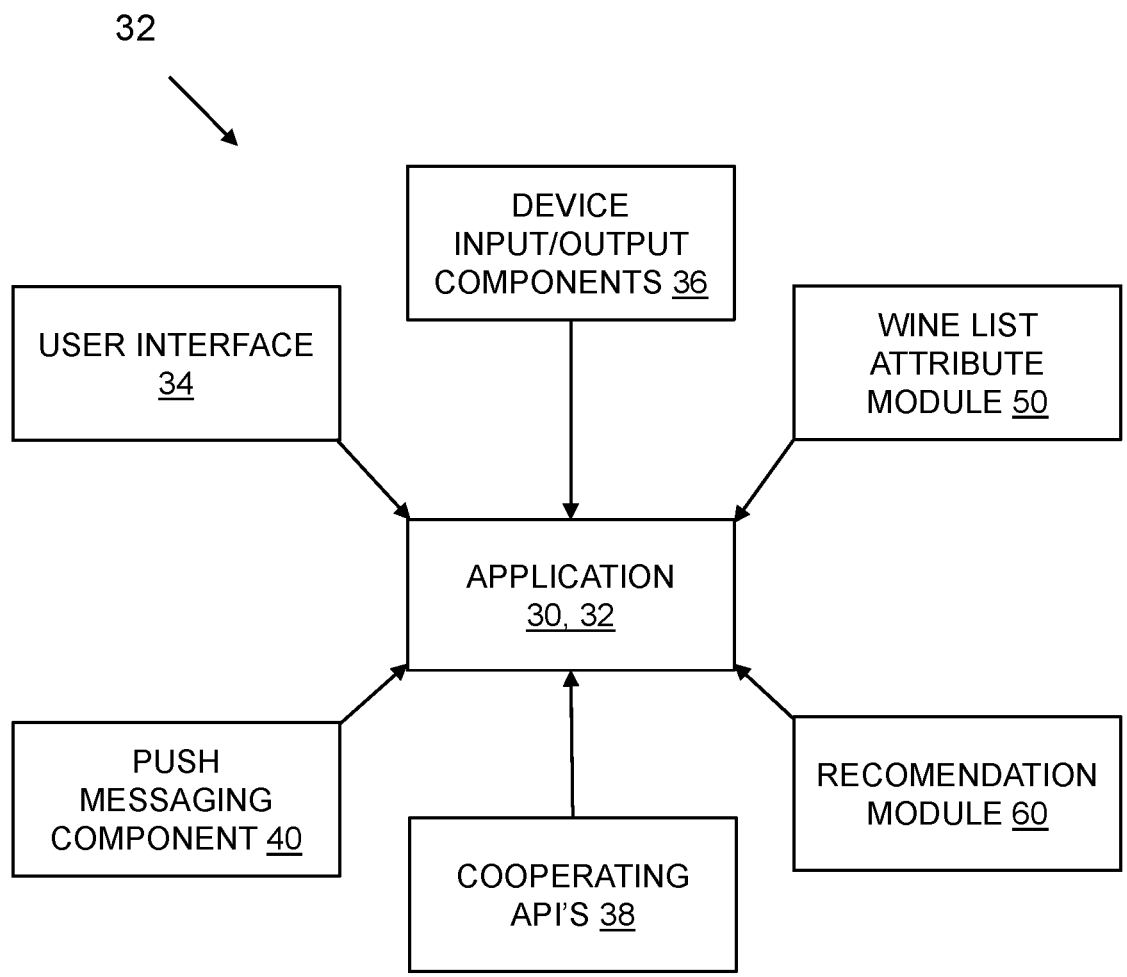
FIG. 4 is a diagram illustrating functional components of a software application for recommending one or more wines implemented by one or portions of the system shown in FIG. 1.
Figure 5:
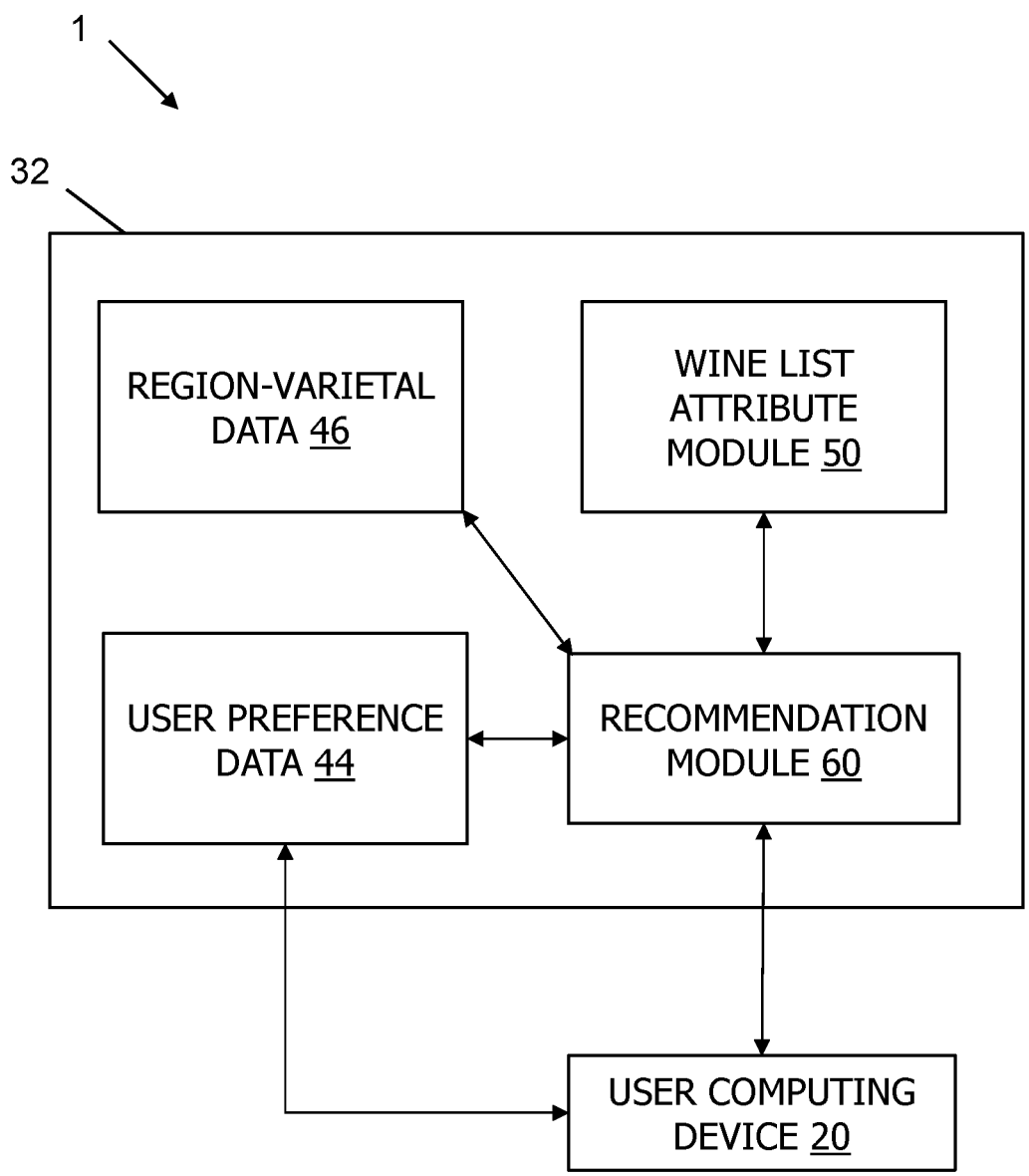
FIG. 5 is a schematic diagram illustrating a software application configured to recommend one or more wines to user, according to an embodiment of the present disclosure.

FIG. 4 is a schematic diagram illustrating various functional components of the software application 30, 32 implemented on one or more computing devices 10 and 20. As illustrated, the software application 30, 32 includes several functional components, including, a user interface 34, device input/output components 36 (e.g. GPS, etc.), wine list attribute module 50, recommendation module 60, cooperating $3^{rd}$ party application programming interfaces 38, and a push messaging system 40. One or more of the functional components illustrated may be used to aid in the acquisition, development, and analysis of wine list and wine preference data. For instance, user interface 34 guides the user through a series of inputs designed to compile user preferences of wine. And wine list attribute module 50 extracts wine attributes from $3^{rd}$ party data sources, such as, for example, wine lists on a given commercial establishment's website or some other retail location. The recommendation module 60 can generate a list of wines extracted from the 3$^{rd}$ party data source that are matched to a user's preferences. One or more of the functional components illustrated in FIG. 5 may be used to implement one or more aspects of the methods described herein on either or both client computing device 20 and server computing device 10. Accordingly, the software applications as described can comprise the client application 30 and the server application 32 such that certain functions may be implemented on the server computing device 10 and other functions may be implemented on the client computing devices 20. Accordingly, for descriptive purposes, the client application 30 and server application 32 may be used interchangeably in the present disclosure.

FIG. 4 illustrates an exemplary software application for recommending a wine to a user. The software application 32 may be implemented primarily on the server computing device 10. However, certain functions may be implemented on a client computing device 10, as described above. The software application 32 may access region-varietal data 46 and user preference data 44. The software application 32 may also include a wine list attribute module 50 and a recommendation module 60. The recommendation module 60 may access the region-varietal data 46, user preference data 44 and wine list data compiled by the wine list attribute module 50.

The region-varietal data 46 includes a database or data store of wines classified according to a geographic hierarchy of regions and varietal types. Regions may include country, states or provinces, sub-regions, down to a wine-growing region. A wine growing region may also be referred to as a base level region. In some cases, a wine-growing region may have one or more aliases. A wine growing region is an identifiable region with unique soil and climate conditions that give rise to a unique taste and aroma characteristics. Local winemaking practices and traditions also factor into these unique flavor and aroma. For instance, a base level region may be the mountain sides of Napa Valley in California, U.S.A. versus the floor of Napa Valley, with each having a specific assigned set of traits. In any event, the lower in a hierarchy regional distinction that a particular wine can be associated with, the more precise flavor and aroma attributes can be predicted. The region-varietal data 46 may be used to establish a unique recommendation to a user. More specifically, the region-varietal data 46 may include a unique identifier for a particular wine, i.e. a fingerprint of a wine. Such an identifier could be used to match a wine to a user's unique and specific preferences, as further explained below.

The region-varietal data 46 includes an indication if a wine is made from a certain varietal. Furthermore, each varietal may be associated with a particular style of wine, e.g. red, white, sparkling, rose, dessert, etc. Styles within a given varietal may have different taste attribute definitions. In the software application, wine grape varietals are defined with specific names corresponding to industry definitions, and include but are not limited to, Cabernet, Merlot, Chardonnay, Sauvignon Blanc, etc. The varietal data will match the names found on wine list data obtained from the Wine Lists. The varietal data may also include one or more aliases for each varietal. The aliases can help matching wine lists with common abbreviations and misspellings, e.g. an alias for Chardonnay may be "Chard" or "Chardonay."

The combination of a wine region and wine varietal is assigned a set of taste attributes which uniquely describes the flavor characteristics of a specific varietal grown in a specific region with specific soil and weather conditions using local wine making techniques. Each region can be associated with one or more wine varietals. As will further described below, the software application as described herein provides a method for characterizing two or more wines made from the same varietal grown and produced in different regions, which have different taste and aroma attributes.

The user preference data 44 may include a trait model for each wine style, e.g. red or white. For example, red wines are defined on a scale of "Earthy" to "Fruity" as well as "Tannic" to "Round." White wines may be defined "Minerally" to "Fruity" and "Rich" to "Acidic." Varietals such as "Chardonnay" can be represented in multiple regions, but their taste attribute traits can vary to account for soil, weather and wine making traditions and styles. The user preference data is obtained from a given user upon initial use of a software application, as will be further described below. For example, user interface 34 guides the user through a series of inputs designed to compile user preferences of wine. User data disclosed herein is exemplary only. It is contemplated that more flavor dimensions can be added to these models for finer resolution of the matching to user taste profiles. Similar attributes will be defined for other wine styles such as, for example, "Sparkling" and "Rose". The data inputs are used to compile a user preference description, based on flavor, aromatic and textural characteristics, which may be used to map directly back to region-varietal trait values of wines, e.g. for substantially all wines produced by the global wine producing market.

Furthermore, the user preference description is based, in part, on persona data. The persona data may include multiple personas for different wine types. For example, there may be multiple red wine personas and multiple white wine personas. In one such example, there may be between 4 and 10 red wine personas and there may be between 4-10 white wine personas. Each user preference description is assigned at least one red wine persona and at least one white wine persona. In a more specific example, however, the user preference description is assigned one red wine persona and one white wine persona. Because the user preference description is mapped back to region-varietal data, and the user preference description is based on the personas data, the wine personas are associated with the region-varietal data for each specific wine. This feature is unique and has not been accomplished heretofore in a technological setting of a recommendation system as described herein.

It should be appreciated that the user traits could be applied to any product where user taste preferences are a consideration, e.g. chocolate, coffee, beer, whisky, cigars. As further described below, the application uses these descriptors of wine characteristics and associates those characteristics with specific regional varietal pairs, as further described herein.

Figure 6:
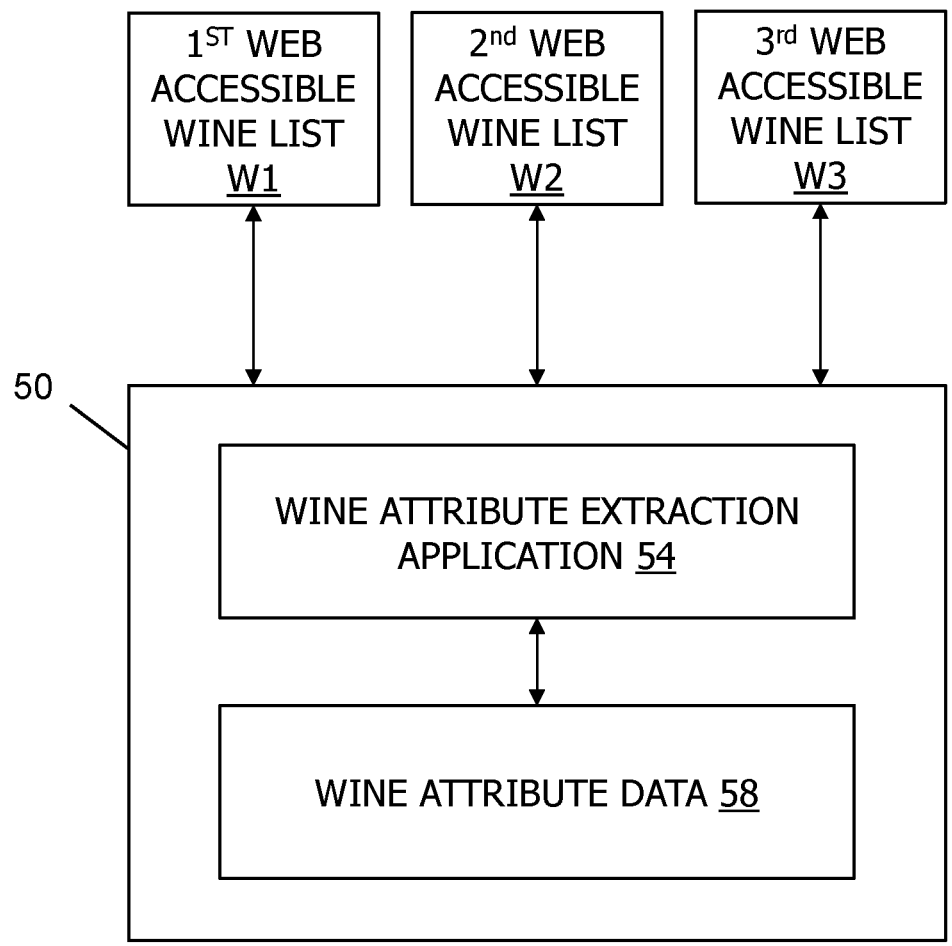
FIG. 6 is a schematic diagram illustrating components of the wine list attribute module according to an embodiment of the present disclosure.

The wine list attribute module 50 is configured to extract wine data from third party data sources for use with the recommendation module 60. As shown in FIG. 6, the wine list attribute module 50 includes a wine attribute extraction application 54 that, when executed, generate wine attribute data 58. The extraction application 54 is configured to access third party data sources. For instance, the extraction application 54 can access, via communications network, a first web accessible wine list W1, a second web accessible wine list W2 and a third web accessible wine list W3. While three wine lists W1, W2, and W3 are shown, the extraction application 54 is configured extract wine data from many more sources than just three. FIG. 6 is intended for illustrative purposes only. The wine list attribute module 50 may be implemented via a process illustrated in FIG. 8 and further discussed below.

Embodiments of the present disclosure assign values or trait parameters to each a region-varietal pair for a particular wine. The assignment of such trait parameters to each region varietal pair links user preference data concerning a particular wine to the taste characteristics of a particular wine obtained from a wine list via the wine attribute module. In other words, the trait parameters assigned to each region-varietal pair links the user preference value to wine attribute data obtained from the wine list. Accordingly, the recommendation application can more accurately predict a favored wine for a particular user because the trait parameters from the user preference data correspond to attributes for a particular wine on a wine list.

Figure 7:
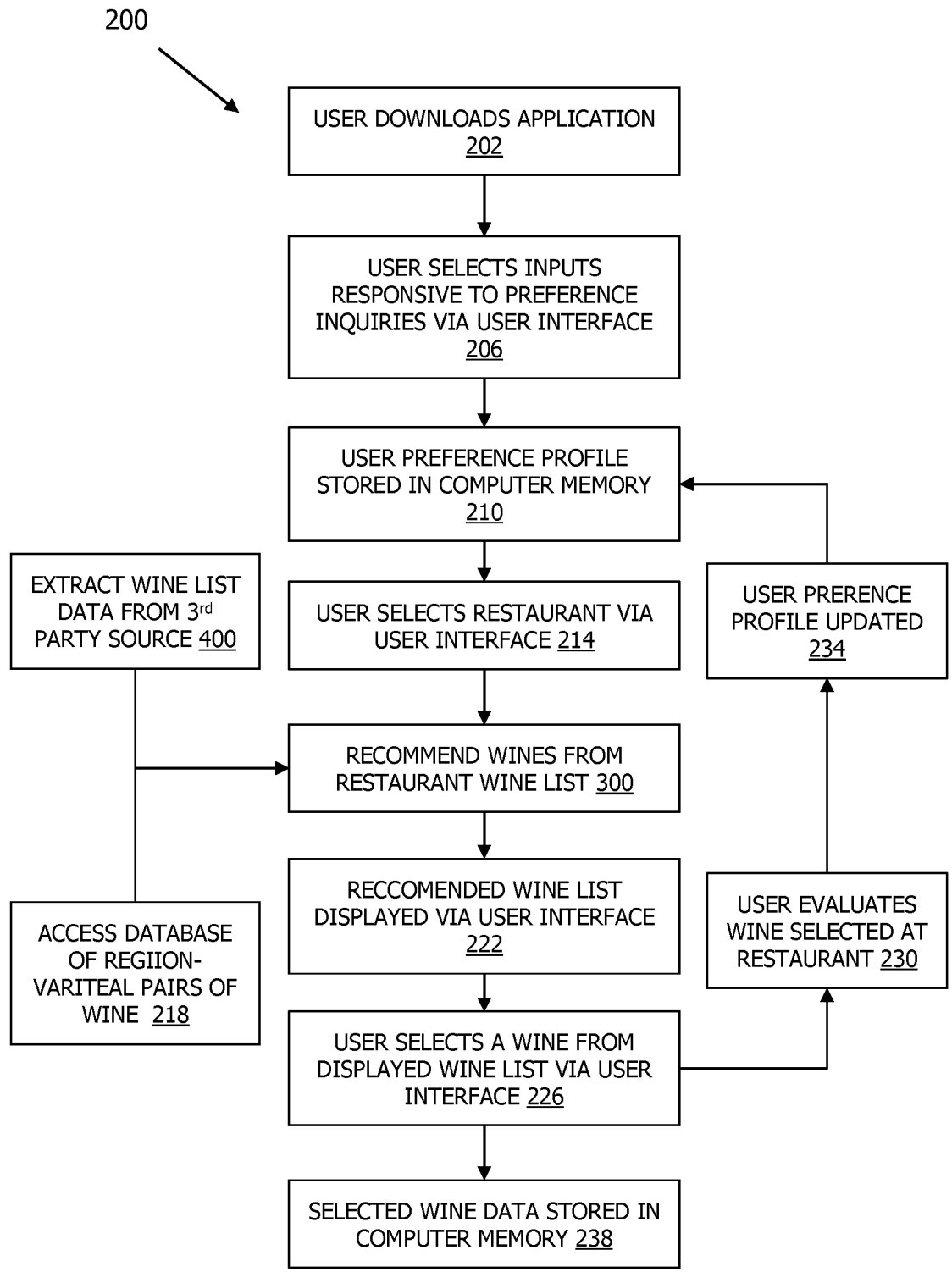
FIG. 7 is a process flow diagram illustrating an exemplary method for generating wine recommendations according to an embodiment of the present disclosure.

Embodiments of the present disclosure includes a process 200 for recommending a wine. As shown in FIG. 7, the process 200 initiates in block 202 when user downloads an application onto his or her respective computing device.

In block 206, a user preference profile for wine is obtained with the software application running on the computing device. More specifically, the user selects inputs responsive to preference inquiries via user interface running on the computing device. Responses to the preference inquiries are used to develop a user preference value. In particular, user inputs from a user may include responses to one or more wine region inquiries and one or more wine varietal inquiries. The method may also include receiving inputs from a user in response to a taste inquiry. The user preference value for each user's regions and varietals preferences are used in other components on the application to aid in recommending a particular wine to a user. In block 210, the user preference profile is stored in computer memory on the user computing device 20 and server computing device 10. The user preference profile may include wine style, price range, serving size, region, varietal, and the user preference value for wine.

In block 214, the user interface is configured to permit selection of a commercial establishment from a map or list of commercial establishments. Process control is transferred to block 300.

In block 300, the software application is configured to recommend one or more wines to a user based on the commercial establishment selected in block 214. While the process is described with respect to selection of one commercial establishment, the software application processes wine information from several different commercial establishments such that, over time, a user to can select a different commercial establishment and be supplied with a recommend list of wines for that commercial establishment. In any event, the recommendation module 50 is configured to recommend a list of wines based on user preference data, wine list data, and regional-varietal database described above, in response to selection of a commercial establishment. According, block 300 may include several separate operations that may occur contemporaneous with selection of the commercial establishment or may occur prior to or even after a user selects a commercial establishment.

The process 200 includes, in block 218, accessing a database of region-varietal pairs of wine. As described above, the region-varietal pairs of wine include a geographic wine region and a wine varietal. The software application accesses the database for development of the recommended wines in block 300.

Block 300 also includes determining an association between the user preference value and one or more of the region-varietal pairs of wine. The method also includes, based on the association between the user preference value and the one or more of the region-varietal pairs of wine, identifying one or more wines from a plurality of wines obtained from a wine list.

The method may also include, in block 400, extracting wine list data from third party data source. In one example, block 400 implements a machine reading module to extract wine attributes for each of the plurality of wines on the wine list. The method may also include, based on the wine attributes for the plurality of wines, matching each of the plurality of wines on the wine list with one or more region-varietal pairs for wine stored in computer memory. The process described in block 400 is further described below.

Once a commercial establishment is selected in block 214, block 300 may also include applying a filter to the list of wines from the commercial establishment selection based on the user preference profile. For example, the process in block 300 may remove all wines that are outside of a given price range for a user. Other filters may include filtering out all wines of a certain varietal. For instance, if a user to does not prefer white wines, white wines are not included any further recommended list of wines.

In addition, block 300 also includes determining a recommendation value for each wine on the wine list. In the embodiment illustrated, the recommendation value is based on a relative variance between a user's preference profile and attributes of each wine on the wine list. For instance, the relative variance is a quantitative parameter between a user's preference value and one or more wine attributes of a wine. A quantitative parameter is a sum of an absolute values of a difference between the user preference value and a trait value for a wine. The recommendation module 50, implementing block 300, may also include removing wines from the wine list where the relative variance between the user's preference value and the one or more attributes of the wine is outside of a predetermined threshold. For example, if the variance is to great such that a user's preference and a wine are too far apart, then those wines are not included a recommended list of wines. Conversely, the recommendation module 50, in block 300 may include compiling a list of recommended wines where variance between the user's preference value and the one or more attributes of the wine is within the predetermined threshold. In such an example, the recommended list of wines is a closer match to the user's preference.

The recommendation module 50, in block 300, is configured to vary the recommended wines by region and varietal. For example, block 300 may include compiling the list of recommended wines includes selecting a first wine with a first variance indicator, a second wine with a second variance indicator, and a third wine with third variance indicator. In this example, the first variance indicator, second variance indicator, and third variance indicator differ from each other such that the first variance indicator indicates a closer match than the third variance indicator. In block 300, the recommendation module 50 can determine if two or more of the first wine, second wine, and third wine are wines within the same geographic region. The method may also include selecting a fourth wine from a different region with a fourth variance indicator if two or more of the first wine, the second wine, and third wine are from the same geographic region. Furthermore, in block 300, the recommendation module may include determining if two or more of the first wine, second wine and third wine are the same varietal of wine. The method may also include selecting a fourth wine from a different varietal with a fourth variance indicator if two or more of the first wine, the second wine, and third wine are the same varietal of wine. The method may also include selecting additional wines for the list of recommended wines up to a predetermined amount. Four variance indicators are described. It should be appreciated that more than four variance indicators may be used.

When a list of wines is compiled with the recommendation module 50 in block 300, process control can be transferred to block 222. In block 222, the recommend wine list is displayed via the user interface running on the user computing device. In block 226, the user can select a wine from the recommended wine list. In addition, in block 230, the user evaluates wine selected at a commercial establishment. In block 234, the user's preference profile is updated based on the user's ratings for the selected wine. The updated user preference profile is stored in computer memory in block 210. Furthermore, selected wine data may be stored in computer memory in block 238.

Figure 8:
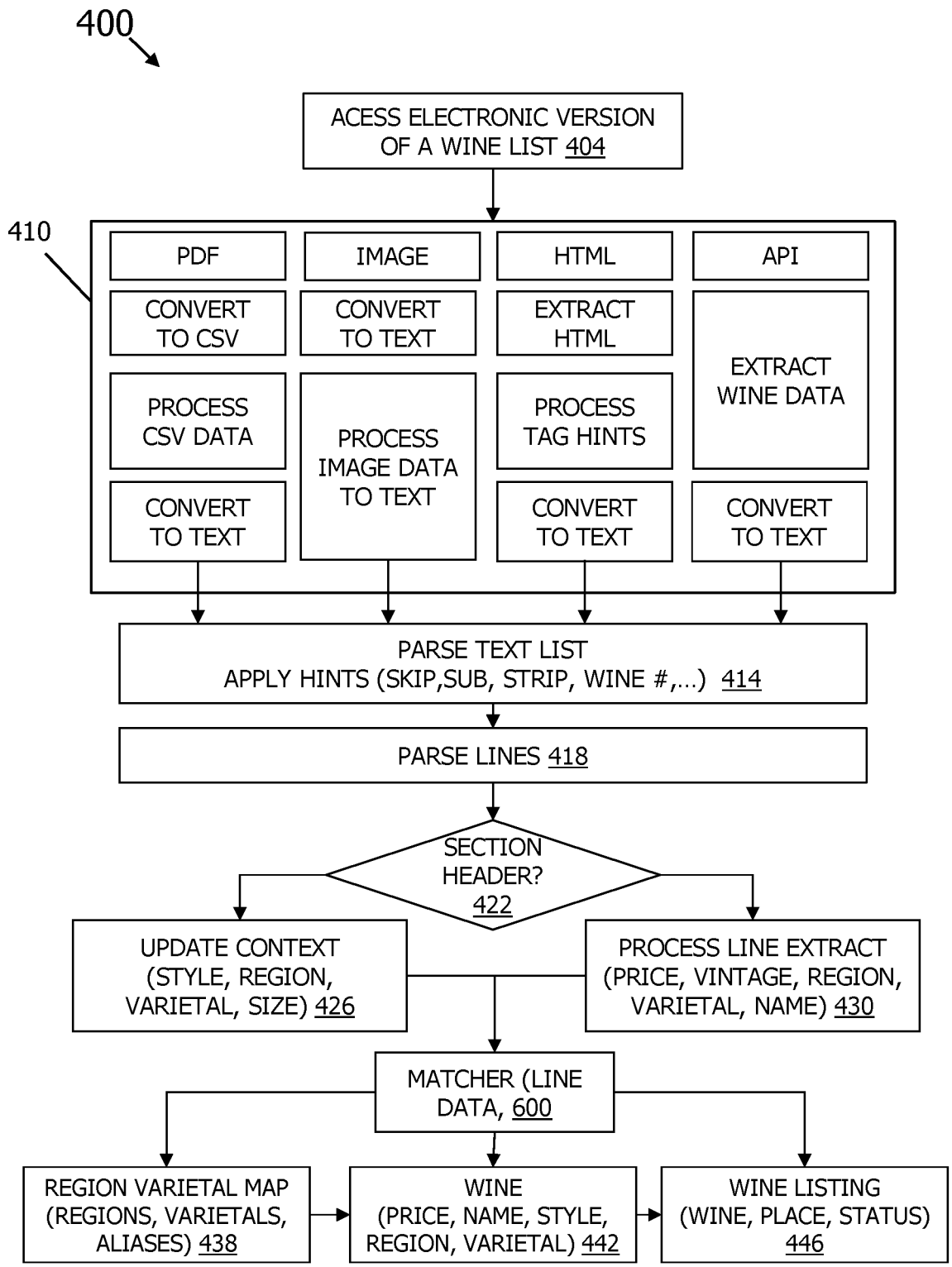
FIG. 8 is a process flow diagram illustrating an exemplary method for extracting wine attributes from $3^{rd}$ party data sources.

As described above, systems and methods as described herein are configured recommend one or more wines based on wine data obtained via communications network. FIG. 8 illustrates an exemplary process for extract item attributes from electronic, web assessable lists, according to an embodiment of the present disclosure. The example shown and described is for accessing and extracting data related to a wine list. However, the method shown in FIG. 8 can be applied to any electronic file that includes a listing of items for human consumption with taste preferences and where regional, and varietal differences are relevant, such as food, coffer, whiskey, cigars, and even *cannabis*. Thus, the described implementation is not limited to strictly access wine data.

The process includes, in block 404, accessing with a communications network an electronic version of the wine list for one or more commercial establishments. Process control is then transferred to block 410. In block 410, an electronic version of the wine list is converted into a wine list text file. As shown, the electronic version of the wine list is a portable file document (PDF), an image file, an html file, or an application programing interface. In each type of wine list source, additional sub operations may occur, as illustrated in block 410. For example, if the electronic version of the wine list is a PDF file, the application converts the characters into a CSV format. The process then further processes the CSV data which is then converted to a wine list text file. If the electronic version of the wine list is an HTML file, then the application extracts the HTML, processes tag hints, and converts the data into a wine list text file. The tag hints may be considered suggestions to the application to help it understand the layout and format of a menu that was only intended to be read by human eyes, as further described below. In this manner, the application is configured to learn layout and context that is typically designed for human communications. If the electronic version of the wine list is an application programming interface (API), then the application extracts wine data and then converts the wine data into a wine list text file. Regardless of the starting file format or data source, the data is converted into wine list text file. Process control is then transferred to block 414.

In block 414, the application parses the wine list text file to into lines of text including wine information. Process control is transferred to block 418. In block 418, the application further parses lines of text into wine attributes for a plurality of wines on the wine list. As described above, the wine attributes include one or more of: a) a region, b) a varietal, c) a vintage d) a name, e) size, and f) a price per size (e.g. glass, bottle, half, magnum). Parsing the wine list text file may also include normalizing a character set of characters contained in the wine list text file.

In block 422, the application determines from the lines of text including wine information if a particular line is a section header. If a particular line is a section header, then process control is transferred to block 426, where context is updated based the lines of text. If, in block 422, the application determines that a particular line is not a section header, then process control is transferred to block 430. In block 430, the application parses lines of text to extract, for each wine of the plurality of wines, a) the region, b) the varietal, c) the vintage d) the name, e) the size, and f) the price.

As described above, the application may utilize hints to aid in parsing the line text. In some instances, however, the increased complexity of the hints necessitated the use of an optional template to streamline the parsing function. Wine lists generally follow a pattern for listing each wine. But sometimes those listings appear in multiple columns and/or are wrapped on multiple lines. Using a template to specify the order of wine listing elements can aid the parser in collecting the pieces of the listing and in determining when one listing ends and the next listing starts.

Accordingly, the parser function of the application is configured to operate in different modes. For example, a template parse hint tells the application how to use implement the template in one of three modes. A first mode may be referred to as the "simple mode" which defaults to an initial parsing method that does not use a template. A second mode may be referred to as the normal mode that does implement a template. In the second or normal mode, the application will use the values specified in the template. A third mode may be referred to as a strict mode. In the third or strict mode, the application is configured to ignore all lines of text that do not match EXACTLY to the template. The strict mode can work well on very complex wine lists.

A template as used herein may have a threefold purpose. First, the template can aid a "multi_line_listings" hint determine where the end of the listing is and where the next one starts. Second, the template can parse the content of listings. For instance, the template can help extract region, varietal, price and different kinds of vintage and multiple parts of the name. The template can also help eliminate extraneous text. Third, the template can help the "dynamic column" hint determine the end of one listing and the start of the next listing within the same line. To work effectively, the template is configured to match what is common among all, or at least most, wines on the list. In general, a tag hint is specified as a list of comma-separated words in the order they should appear in a listing, and optionally a slash. The template is a structure for analyzing characters and provide a framework for the parser to extract information from the text. For example, template=region,varietal,price/vintage, name Exemplary valid word values include (but are not limited to) region, varietal, price, name, junk, vintage, etc. In this context, these exemplary word values may be defined as follows: "region" means some region in the database (or aliases); "varietal" means some varietal in the varietal database (or aliases); "price" is the price or prices; "name" is text to be considered part of the name (can appear more than once in template).

In another example, the template may include a "junk" word value. "Junk" is text to be ignored in parsing and/or omitted from wine name. "Junk" can be used to signal that an important item is not the first or last item on the line even though the application does not know what is there. The junk word value also useful for removing training text from the name. For example: 'a fruity, robust wine that my friend has made in his bathtub.' If junk and wine name are next to each other, this won't work because name could be any format and set of words. In contrast, if junk is next to varietal, the application knows to stop at the varietals the database recognizes.

"Vintage" word value in the template that means the vintage. In some cases, the vintages may be different character or digits. For instance, "vvvv" is used for four digit vintages only; "avv" is used for two digits with a preceding apostrophe, "vv" is used for two or four digit vintage with no identifying apostrophe. This word value may use position to decide if it is a price or vintage In another example, "Question Mark '?" may be used in the template. For instance, if a template parse type is "strict", then a template item can be specified as optional in a given position. For example, the varietal may appear before or after the region. " . . . varietal?, region, varietal? . . . ". This means the strict template will not fail if the varietal is not found in the first position. In embodiments using the template "a slash "/" may be used to separate everything that must be on the first line from those that must be on the last line. The template may include a "size" word value that means a qualifier for price. It indicates bottle size, e.g. bottle, glass, half, full, magnum, 375 ml, 1 L, or other size specifiers. In one example, the template is used right to left to fill in items that can be parsed and then the regular matching fills in any remaining items.

The parser function may include other hints. For example, the parser may include a "dynamic columns hint." The dynamic column hint is active only when "dynamic columns" is specified as a separate hint. The template is used in this way to signal what is last on each line or first on each line. These may be prioritized as follows: vintage starts the first line and price ends either the first or last line. There may be other hints as well.

In another example, the parser function may use a "multi-line hint." The multi-line hint is intended to merge the pieces of a wine listing which appear on multiple lines. The template is used to know when to stop processing one listing and start collecting the next. For example, if the template has a slash, the application forces the multi-line hint to go to as many lines as specified or a maximum number of lines specified. Regardless, in block 430 the application parses lines of text to extract, using the methods described above.

From either block 426 or block 430, process control is transferred to block 600, where the wine attributes are matched to a region-varietal pair in a matching operation. More specifically, in block 600, the application matches each of the plurality of wines on the wine list with one or more region-varietal pairs for wine stored in computer memory. The match is based, in part, on the wine attributes for the plurality of wines extract from the wine list.

In one example, the matching operation may include implementing a sequence of context match operations between the wine attributes in the lines of text list and one or more region-varietal pairs of wine in a database of region-varietal pairs of wine.

In such an example, the sequence of context match operations further comprise a first operation that includes 1) identifying a) region and varietal from a line of the lines of text and b) a style from Identifying a) region and varietal from a line of the lines of text and b) a style from header context; 2) determining if a match exists in the region-varietal database based on a) and b); and 3) if no match exists, transferring process control to the next match operation.

The second match operation may also include 1) identifying a) region and varietal from the line of the lines of text, and b) a style word in the line; 2) determining if a match exists in the region-varietal database based on based on a) and b); and 3) if no match exists, transferring process control to the next match operation.

The third match operation may also include 1) identifying a) region and varietal from the line of text, and b) identify a style from varietal data; 2) determining if a match exists in the database of region-varietal pairs of wine; and 3) if no match exists, transferring process control to the next match operation.

The fourth match operation may include 1) determining if the line includes a singular region and identifying a white wine style first; 2) determining if a match exists in the database of region-varietal pairs of wine, and 3) if no match exists, transferring process control to the next match operation.

The fifth match operation may also include 1) identifying a region and varietal from the line and use a header varietal to determine the style; 2) determining if a match exists in the database of region-varietal pairs of wine, and 3) if no match exists, transferring process control to the next match operation.

The sixth match operation may also include 1) identifying a varietal from the line and use style and region from the header context; 2) determining if a match exists in the database of region-varietal pairs of wine; and 3) if no match exists, transferring process control to the next match operation.

The seventh match operation may also include 1) identifying a region from the line and use style and varietal from the header context; 2) determining if a match exists in the database of region-varietal pairs of wine; and 3) if no match exists, transferring process control to the next match operation.

The eighth match operation may also include 1) identifying a style, region and varietal from the header context; 2) determining if a match exists in the database of region-varietal pairs of wine; and 3) if no match exists, transferring process control to the next match operation.

The ninth match operation may include 1) identifying a region and varietal from the line and use style from last match; 2) determining if a match exists in the database of region-varietal pairs of wine; and 3) if no match exists, transferring process control to the next match operation.

The tenth match operation may include 1) determining if the line includes a singular region and identify a red wine style; 2) determining if a match exists in the database of region-varietal pairs of wine; and 3) if no match exists, transferring process control to the next match operation. The results of the match operations are wine attribute data for several wines included in the electronic wine list that are matched to a region-varietal pairs in the database described above.

With the wine attributes matched to the region-varietal pairs, and the use preferences associated with the wine varietal pairs, the application can recommend a set of wines with a high likelihood of falling within the user's desired wine tastes and preferences. Furthermore, the recommended list is specific to a commercial establishment and may be updated in real time.

Wine lists changes over time. The application is configured to determine to extent of wine list change and updated the data profiles as needed. The methods and applications described herein therefore include storing in computer memory a first electronic version of the web accessible wine list. The method may also include, after storing in computer memory the first electronic version of the wine list, accessing again with the communications network the web accessible wine list. The method includes storing in computer memory a second electronic version of the web accessible wine list. The method may also include comparing the second electronic version of the web accessible wine list with the first electronic version of the web accessible wine list. Then, the method determines if there is any variance between the second electronic version of the web accessible wine list and the first electronic version of the web accessible wine list. The method also includes extracting wine attributes from a plurality of wines contained in the web accessible wine list if there is a variance between the second electronic version of the web accessible wine list and the first electronic version of the web accessible wine list. Thus, as the wine lists changes, the wine attribute data for a wine list is updated from time to time as needed.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in an order as desired.

The invention claimed is:

1. A method, comprising:
 obtaining, via a graphical user interface running on a client computing device, a user preference profile for wine wherein the user preference profile includes a user preference value for one or more geographic wine regions and one or more wine varietals or blends of varietals produced within a region;
 accessing, with a communications network, a database of region-varietal wine data stored in a memory of a back-end computing device, the region-varietal data including multiple wines classified according to a geographic hierarchy of wine region and varietals, wherein the geographic hierarchy of wine region and varietals includes a country, a sub-region within the country, and a base-level region within a sub-region of the country, wherein the base-level region is an identifiable region with unique soil conditions, unique climate conditions, unique wine aroma, and unique wine taste;
 compiling, with a computer processor, the user preference value for the user preference profile into the memory unit of the back-end computing device or the client computing device;
 obtaining, via a communications network, an electronic data file of a wine list of a commercial establishment, wherein the electronic data file of the wine list is stored in the memory of the back-end computing device; and
 determining, via the computer processor, a recommendation value for each of the plurality of wines from the wine list, wherein the recommendation value is based on a relative variance between a user's preference profile and attributes of each one of multiple wines from the wine list, wherein the relative variance is a quantitative parameter indicative of a difference between a user's preference value and the attributes of a particular wine, wherein the quantitative parameter is a sum of absolute values of the difference between the user preference value and the attributes of a particular wine;
 compiling, with the computer processor, a list of recommended wines where the relative variance between the user's preference value and the attributes of the wine is within a predetermined threshold;
 removing, with the computer processor, wines from the list of recommended wines where the relative variance between the user preference value and the attributes of a particular wine is outside of the predetermined threshold; and
 causing the display, via the graphical user interface, of the list of recommend wines on the client computing device.

2. The method of claim 1, further wherein the user preference profile includes a wine style, a price range, a serving size, a geographic wine region, and a wine varietal.

3. The method of claim 1, wherein each wine of the plurality of wines of the wine list include wine attributes, wherein the wine attributes includes a wine style, a price range, a serving size, a geographic wine region, and a wine varietal.

4. The method of claim 1, wherein obtaining the user preference profile further comprises receiving inputs, via the graphical user interface, based on one or more region and wine varietal pairs.

5. The method of claim 1, wherein obtaining the user preference profile further comprises receiving inputs, via the graphical user interface, responsive to one or more wine region inquiries.

6. The method of claim 1, wherein obtaining the user preference profile further comprises receiving inputs, via the graphical user interface, to one or more wine varietal inquiries.

7. The method of claim 1, wherein obtaining the user preference profile further comprises receiving inputs, via the graphical user interface, responsive to one or more taste inquiries.

8. The method of claim 1, further comprising:
 receiving inputs indicative of a selection of the commercial establishment;
 applying a filter to wines in the wine list from the selected commercial establishment, based on the user preference profile; and
 based on the filter, compiling a preliminary list of recommended wines, wherein the preliminary list of recommended wines includes the multiple wines obtained from the plurality of wines of the wine list.

9. The method of claim 1, further comprising displaying with a graphical user interface the one or more wines of the plurality of wines obtained from the wine list of the commercial establishment.

10. The method of claim 1, wherein compiling the list of recommended wines includes selecting a first wine with a first variance indicator, a second wine with a second variance indicator, and a third wine with third variance indicator, wherein the first variance indicator, the second variance indicator, and the third variance indicator differ from each other.

11. The method of claim 10, further comprising:
 determining if two or more of the first wine, the second wine, and the third wine are wines with the same geographic region; and
 if two or more of the first wine, the second wine, and the third wine are from the same geographic region, selecting a fourth wine from a different geographic region with a fourth variance indicator.

12. The method of claim 10, further comprising:
determining if two or more of the first wine, second wine and third wine are the same varietal of wine; and
if two or more of the first wine, the second wine, and the third wine are the same varietal of wine, selecting a fourth wine from a different varietal with a fourth variance indicator.

13. The method of claim 10, further comprising:
determining if two or more of the first wine, second wine and third wine are the same geographic region and varietal of wine; and
if two or more of the first wine, the second wine, and the third wine are the same geographic region and varietal of wine, selecting a fourth wine from a different geographic region and varietal having with a fourth variance indicator.

14. The method of claim 1, further comprising selecting additional wines for the list of recommended wines up to a predetermined amount.

15. The method of claim 1, wherein compiling the list of recommended wines includes selecting multiple wines such that each wine is from a different geographic wine region and is a different wine varietal.

16. The method of claim 1, further comprising implementing a machine reading module to extract attributes for the plurality of wines on the wine list.

17. The method of claim 16, wherein implementing the machine reading module to extract wine attributes for the plurality of wines on the wine list comprises:
accessing with a communications network an electronic version of the wine list for one or more commercial establishments;
converting the electronic version of the wine list into a wine list text file;
parsing the wine list text file to into lines of text including wine information;
parsing the lines of text into wine attributes for a plurality of wines on the wine list, wherein the wine attributes include a) a region, b) a varietal, c) a vintage d) a name, e) a size, and f) a price; and
based on the wine attributes for the plurality of wines, matching each of the plurality of wines on the wine list with one or more region-varietal pairs for wine stored in computer memory, wherein each region-varietal pair includes a geographic wine region and a wine varietal.

18. A system, comprising:
a first computing device including a memory unit and a computer processor;
a database of region-varietal wine data stored in the memory unit, the region-varietal data including multiple wines classified according to a geographic hierarchy of wine region and varietals, wherein the geographic hierarchy of wine region and varietals includes a country, a sub-region within the country, and a base-level region within a sub-region of the country, wherein the base-level region is an identifiable region with unique soil conditions, unique climate conditions, unique wine aroma, and unique wine taste;
a software application executed by the computer processor of the first computing device that is configured to:
obtain a user preference profile for wine in response to inputs into a second computing device in electronic communication via a communications network with the first computing device, wherein the user preference profile includes a user preference value for one or more geographic wine regions and one or more wine varietals;
compile the user preference value for the user preference profile obtained from the second computing devices into the memory unit of the first computing device;
compile electronic data from an electronic data file of a wine list of a commercial establishment, wherein the electronic data file of the wine list is obtained via a communications network and is stored in the memory unit of the first computing device;
determine, via the computer processor, a recommendation value for each of the plurality of wines from the wine list, wherein the recommendation value is based on a relative variance between a user's preference profile and attributes of each of the plurality of wines from the wine list, wherein the relative variance is a quantitative parameter indicative of a difference between a user's preference value and the attributes of a particular wine, wherein the quantitative parameter is a sum of an absolute values of the difference between the user preference value and the attributes of a particular wine;
compile a list of recommended wines where the relative variance between the user's preference value and the attributes of the wine is within a predetermined threshold;
remove wines from the list of recommended wines where the relative variance between the user preference value and the attributes of a particular wine is outside of the predetermined threshold; and
cause the display, via the graphical user interface, of the list of recommend wines on the second computing device.

19. The system of claim 18, wherein the user preference profile includes a wine style, a price range, a serving size, a geographic wine region, and a wine varietal.

20. The system of claim 18, wherein the region varietal data further includes wine attributes including a wine style, a price range, a serving size, the base-level region of wine, and a wine varietal.

21. The system of claim 18, wherein the software application is configured to receive inputs based on one or more region and wine varietal pairs.

22. The system of claim 18, wherein the software application is configured to, in obtaining the user preference profile, to receive inputs responsive to one or more wine region inquiries.

23. The system of claim 18, wherein the software application is configured to, in obtaining the user preference profile, to receive inputs responsive to one or more wine varietal inquiries.

24. The system of claim 18, wherein the software application is configured to, in obtaining the user preference profile, to receive inputs responsive to one or more taste inquiries.

25. The system of claim 18, further comprising a graphical user interface configured to receive inputs indicative of a selection of the commercial establishment;
wherein the software application is configured to 1) apply a filter to wines in the wine list from the selected commercial establishment, based on the user preference profile, and 2) based on the filter, compile a preliminary list of recommended wines, wherein the preliminary list of recommended wines includes multiple wines obtained from the plurality of wines of the wine list.

26. The system of claim 18, further comprising a graphical user interface configured to display multiple wines of the plurality of wines obtained from the wine list of the commercial establishment.

27. The system of claim 18, wherein the software application is configured to compile the list of recommended wines includes selecting a first wine with a first variance indicator, a second wine with a second variance indicator, and a third wine with third variance indicator, wherein the first variance indicator, the second variance indicator, and the third variance indicator differ from each other.

28. The system of claim 27, wherein the software application is configured to:
   determine if two or more of the first wine, the second wine, and the third wine are wines with the same geographic region; and
   if two or more of the first wine, the second wine, and the third wine are from the same geographic region, select a fourth wine from a different geographic region with a fourth variance indicator.

29. The system of claim 27, wherein the software application is configured to:
   determine if two or more of the first wine, second wine and third wine are the same varietal of wine; and
   if two or more of the first wine, the second wine, and the third wine are the same varietal of wine, select a fourth wine from a different varietal with a fourth variance indicator.

30. The system of claim 27, wherein the software application is configured to:
   determine if two or more of the first wine, second wine and third wine are the same geographic region and varietal of wine; and
   if two or more of the first wine, the second wine, and the third wine are the same geographic region and varietal of wine, select a fourth wine from a different geographic region and varietal having with a fourth variance indicator.

31. The system of claim 18, wherein the software application is configured to further select additional wines for the list of recommended wines up to a predetermined amount.

32. The system of claim 18, wherein the software application is configured to implement a machine reading module to extract attributes for the plurality of wines on the wine list.

33. The system of claim 32, wherein the software application is configured to, in implementing the machine reading module to extract wine attributes for the plurality of wines on the wine list,
   access with a communications network an electronic version of the wine list for one or more commercial establishments;
   convert the electronic version of the wine list into a wine list text file;
   parse the wine list text file to into lines of text including wine information;
   parse the lines of text into wine attributes for a plurality of wines on the wine list, wherein the wine attributes include a) a region, b) a varietal, c) a vintage d) a name, e) a size, and f) a price; and
   based on the wine attributes for the plurality of wines, matching each of the plurality of wines on the wine list with one or more region-varietal pairs for wine stored in computer memory, wherein each region-varietal pair includes a geographic wine region and a wine varietal.

34. The system of claim 18, further comprising a computer processer configured to execute the software application.

35. A method, comprising:
   obtaining, via a graphical user interface running on a client computing device, a user preference profile for wine, wherein the user preference profile includes a user preference value for one or more geographic wine regions and one or more wine varietals;
   accessing, with a communication network, a database of region-varietal pairs of wine stored in a memory unit of a back-end computing device, wherein the region-varietal pair of wine includes a geographic wine region and a wine varietal;
   compiling, with a computer processor, the user preference value for the user preference profile into the memory unit of the back-end computing device;
   determining, with the computer processor of the back-end computing device, which executes instructions of a software application running on the back-end computing device, an association between the user preference value and at least one of the region-varietal pairs of wine;
   based on the association between the user preference value and the at least one of the region-varietal pairs of wine, identifying, via the computer processor of the back-end computing device, one or more wines from a plurality of wines obtained from a wine list of a commercial establishment;
   implementing, via the computer processor of the back-end computing device, a machine reading module to extract attributes for the plurality of wines on the wine list in the electronic data file of the wine list, wherein implementing the machine reading module to extract wine attributes for the plurality of wines on the wine list further comprises:
   accessing, via a communications network, an electronic version of the wine list for one or more commercial establishments;
   converting, via the computer processor, the electronic version of the wine list into a wine list text file;
   parsing, via the computer processor, the wine list text file to into lines of text including wine information;
   parsing via the computer processor, the lines of text into wine attributes for a plurality of wines on the wine list, wherein the wine attributes include a) a region, b) a varietal, c) a vintage d) a name, e) a size, and f) a price; and
   based on the wine attributes for the plurality of wines, matching, via the computer processor, each of the plurality of wines on the wine list with one or more region-varietal pairs for wine stored in computer memory, wherein each region-varietal pair includes a geographic wine region and a wine varietal.

36. The method of claim 35, further comprising:
   receiving inputs indicative of a selection of the commercial establishment;
   applying a filter to wines in the wine list from the selected commercial establishment, based on the user preference profile; and
   based on the filter, compiling a preliminary list of recommended wines, wherein the preliminary list of recommended wines includes the one or more wines obtained from the plurality of wines of the wine list.

37. The method of claim 36, further comprising displaying with a user interface the one or more wines of the plurality of wines obtained from the wine list of the commercial establishment.

38. A system, comprising:

a first computing device including a memory unit and a computer processor, the memory unit including stored thereon a database of region-varietal pairs of wine, wherein the region-varietal pair of wine includes a geographic wine region and a wine varietal; and a software application, executable by the computer processor of the first computing device, and configured to:

obtain a user preference profile for wine with a software application, wherein the user preference profile includes a user preference value for one or more geographic wine regions and one or more wine varietals;

determine an association between the user preference value and at least one of the region-varietal pairs of wine;

based on the association between the user preference value and the at least one of the region-varietal pairs of wine, identify one or more wines from a plurality of wines obtained from a wine list of a commercial establishment or retail location;

implement a machine reading module to extract attributes for the plurality of wines on the wine list, wherein the machine reading module is further configured to 1) access with a communications network an electronic version of the wine list for one or more commercial establishments, 2) convert the electronic version of the wine list into a wine list text file; 3) parse the wine list text file to into lines of text including wine information; 4) parse the lines of text into wine attributes for a plurality of wines on the wine list, wherein the wine attributes include a) a region, b) a varietal, c) a vintage d) a name, e) a size, and f) a price; and based on the wine attributes for the plurality of wines, matching each of the plurality of wines on the wine list with one or more region-varietal pairs for wine stored in computer memory, wherein each region-varietal pair includes a geographic wine region and a wine varietal.

39. The system of claim 38, further comprising a graphical user interface configured to display the one or more wines of the plurality of wines obtained from the wine list of the commercial establishment.

40. The system of claim 39, wherein the software application is configured to, in identifying the one or more wines from the plurality of wines obtained from the wine list of the commercial establishment, determine a recommendation value for each of the plurality of wines from the wine list, wherein the recommendation value is based on a relative variance between a user's preference profile and attributes of each of the plurality of wines from the wine list.

* * * * *